United States Patent [19]
Levy

[11] Patent Number: 5,232,366
[45] Date of Patent: Aug. 3, 1993

[54] CUTTING PHYSIOLOGIC TISSUES

[75] Inventor: Guy Levy, Tustin, Calif.

[73] Assignee: Laser Medical Technology, Inc., San Clemente, Calif.

[21] Appl. No.: 851,197

[22] Filed: Mar. 13, 1992

Related U.S. Application Data

[60] Division of Ser. No. 784,978, Oct. 30, 1991, Pat. No. 5,118,293, which is a division of Ser. No. 615,789, Nov. 20, 1990, Pat. No. 5,092,773, which is a continuation-in-part of Ser. No. 299,472, Jan. 19, 1989, Pat. No. 5,020,995, and a continuation-in-part of Ser. No. 351,203, May 15, 1989, which is a continuation-in-part of Ser. No. 335,245, Apr. 10, 1989, abandoned.

[30] Foreign Application Priority Data

Dec. 21, 1988 [FR] France .................. 8817549

[51] Int. Cl.$^5$ .................................... A61C 5/00
[52] U.S. Cl. .................................. 433/215; 606/3
[58] Field of Search .............. 606/2, 3, 10, 11, 12, 606/15, 16; 433/215, 29

[56] References Cited

U.S. PATENT DOCUMENTS

| | | |
|---|---|---|
| 3,769,963 | 11/1973 | Goldman et al. |
| 4,408,602 | 10/1983 | Nakajima ............................ 606/10 |
| 4,791,927 | 12/1988 | Menger .................................. 606/3 |
| 5,125,922 | 6/1992 | Dwyer et al. .......................... 606/3 |
| 5,139,494 | 8/1992 | Freiberg .............................. 606/15 |

Primary Examiner—Cary E. O'Connor
Attorney, Agent, or Firm—Spensley Horn Jubas & Lubitz

[57] ABSTRACT

A method of cutting physiologic tissue in the mouth of a patient, comprising: providing a tunable laser which is tunable to produce laser radiation at any one of at least two different wavelengths, including a first wavelength which is effective for cutting physiologic tissue of a first type and a second wavelength for cutting physiologic tissue of a second type; tuning the laser to produce radiation at one first and second wavelengths; emitting the radiation being produced by the laser and directing the emitted radiation at physiologic tissue of the type corresponding to the radiation wavelength which the laser is tuned to produce; and at least when the laser is tuned to produce radiation at a selected wavelength, directing a cooling liquid at the physiologic tissue at which the emitted radiation is being directed simultaneously with performance of the directing step.

10 Claims, 1 Drawing Sheet

CUTTING PHYSIOLOGIC TISSUES

CROSS REFERENCE TO RELATED APPLICATIONS

This is a division of application Ser. No. 07/784,978 filed on Oct. 30, 1991, now U.S. Pat. No. 5,118,293, which is a division of application Ser. No. 07/615,789 filed Nov. 20, 1990, now U.S. Pat. No. 5,092,773, which is a continuation-in-part of application Ser. No. 07/299,472 filed Jan. 19, 1989, now U.S. Pat. No. 5,020,995, and application Ser. No. 07/351,203 filed May 15, 1989, itself a continuation-in-part of application Ser. No. 07/335,245, filed Apr. 10, 1989, now abandoned. These applications are incorporated herein by reference.

BACKGROUND OF THE INVENTION

The present invention relates to the use of laser radiation for treating mineralized body tissues, including in particular a variety of dental tissues and bone.

The prior applications, cited above, disclose procedures and devices for cutting or vaporizing mineralized physiologic tissues, including particularly enamel, dentin, cementum and bone, using laser radiation. It has been found that such operations can be performed with laser radiation at wavelengths which are strongly absorbed by hydroxyapatite, which is a principal constituent of such physiologic tissues, and is only weakly absorbed by water. The preferred source of laser radiation is a Nd:YAG laser since its normal wavelength of $1.06\mu$ satisfies these requirements in a particularly suitable manner.

The prior applications also disclose the possibility of performing treatments in tooth root canals by delivering laser radiation via an optical fiber which is introduced into the canal. Such a fiber can also be disposed to permit the laser radiation to perform various treatments at a root apex.

Techniques for filling cavities or other openings in tooth or bone material, using laser radiation to effect fusion of the filling material, have also been previously disclosed.

As a result of further investigations, a number of significant improvements in these procedures have been discovered, and these improvements are the subject of the present application.

SUMMARY OF THE INVENTION

Accordingly, it is an object of the present invention to improve the effectiveness with which the types of tissues described above can be cut or vaporized by such laser radiation.

Another object of the invention is to facilitate the widening of tooth canals by such laser radiation.

Still another object of the invention is to provide improved fillings or coatings for root canals, tooth cavities and cracks or fissures in tooth material, including the roots thereof, and bone material.

A further object of the invention is perform various operations on metal bodies in the mouth.

The above and other objects are achieved, according to the present invention, by a method of cutting mineralized physiologic tissue, including tooth enamel and dentin and bone, comprising: producing laser radiation at a wavelength which is absorbed more strongly by hydroxyapatite than by water; linearly polarizing the radiation and forming the radiation into a small diameter beam; and applying the polarized beam to a surface of tissue to be cut so that the beam has a selected angle of incidence relative to the surface; wherein the radiation is polarized and the beam is directed so that the radiation impinging on the surface has a polarization P parallel to the surface.

Objects of the invention are further achieved, in a device for removing physiologic tissue from a tooth canal by application to the tissue of laser radiation, which device includes a source of such laser radiation and an optical fiber having a proximal end disposed to receive the radiation and a distal end dimensioned to be insertable into the tooth canal, by giving the optical fiber a tapered shape in a region adjacent the distal end such that the diameter of the fiber decreases in the direction toward the distal end.

Additional objects of the invention are achieved by a method of filling or coating mineralized physiologic tissue, including tooth enamel and dentin and bone, with a calcium containing product capable of being bonded to a surface of the tissue, by providing two starting components which when combined and exposed to light of a selected wavelength undergo a photochemical reaction to form the calcium containing product, projecting the components toward the surface, and causing light of the selected wavelength to impinge on the components at least partially before the components reach the surface in order to create the photochemical reaction and cause the resulting calcium containing product to bond to the tissue.

Further objects of the invention are achieved by a method of filling a prepared tooth canal in order to seal the canal, by providing an optical fiber containing silica, having a low melting temperature and dimensioned to be insertable in the canal, inserting the fiber into the canal so that the fiber extends along the region to be filled, and conducting through the fiber optical radiation of a wavelength and energy level sufficient to melt a portion of the fiber which is in the canal and to cause silica in the fiber to bond to the canal wall.

Additional objects of the invention are achieved by a method of destroying bacteria on tooth surfaces by staining the bacteria to cause the bacteria to have a dark coloration, and exposing the stained bacteria to laser radiation at a wavelength and energy level sufficient to destroy the bacteria.

In further accordance with the invention, the type of laser radiation described herein can be used to fuse, i.e. melt or weld, or vaporize metal bodies secured to bone or tooth tissue, including gum tissue, or located in a tooth canal. This opens the possibility of conveniently installing, removing, or shaping metal implants and easily eliminating broken file tips lodged in a tooth canal. These operations must be performed in conjunction with a cooling liquid spray or stream to prevent charring or burning of adjacent tissue.

Other objects of the invention are achieved by a handpiece for directing laser radiation onto physiologic tissue, comprising: a housing; fiber holding means in the housing for removably retaining an optical fiber in order to deliver radiation to one end of the fiber and to allow the other end of the fiber to protrude out of the housing and to emit the radiation; and an optical fiber inserted, and removably retained, in the fiber holding means. To fully achieve the objects of the invention, the handpiece is further provided with a tube or comparable structure for delivering a stream or spray of cooling liquid, preferably water or a cooling and cleaning solution employed in dentistry, to the region at which the radiation is directed.

Still other objects of the invention will be achieved by various combinations of the objects and features described above, as will become apparent to those skilled in the art from the following detailed description.

DESCRIPTION OF THE PREFERRED EMBODIMENTS

According to a first aspect of the present invention, improved control over cutting actions is achieved by the use of polarized laser radiation having a polarization P.

Figure 1:
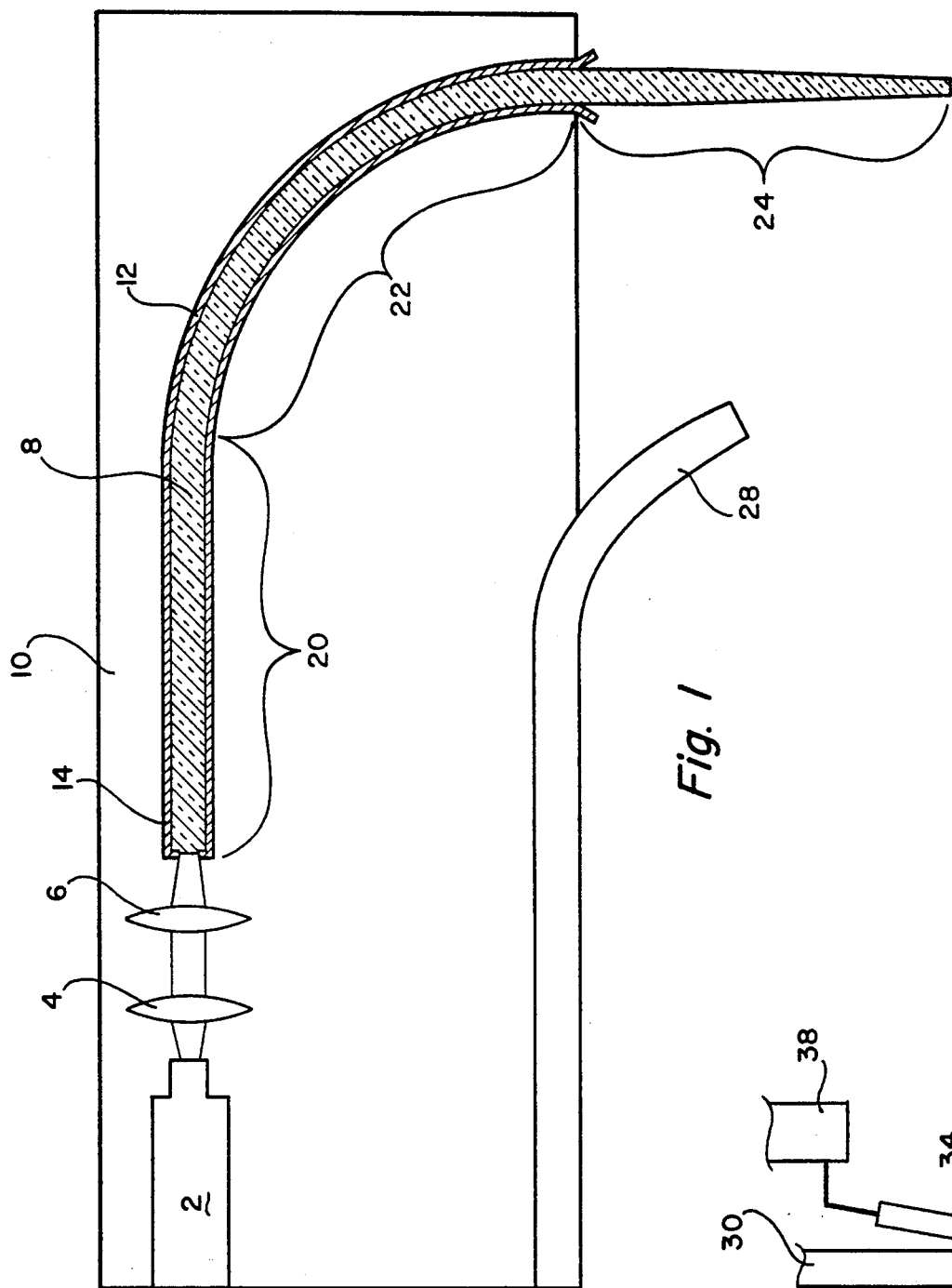
FIG. 1 is a side elevational view illustrating the basic components of a device constructed to perform various treatments according to the invention.

One exemplary embodiment of a system for producing such a polarized beam is shown in FIG. 1. Radiation emitted from an Nd:YAG laser 2 is collimated by a converging lens 4. Then, a suitably constructed lens 6 both linearly polarizes the resulting collimated beam and converges the polarized beam into the entrance end of an optical fiber 8. Fiber 8 passes through handpiece 10 and extends out of handpiece 10 by an amount needed to bring the free end of fiber 8 to the tissue region to be treated.

Since such optical fiber can experience erosion of its distal end during use, it is desirable that fiber 8 be installed in handpiece 10 in a manner to be easily replaceable. This can be achieved most simply by providing handpiece 10 with a fiber guide channel 12 into which fiber 8 can be inserted, and from which it can be withdrawn, but which will gently grip the fiber while accurately positioning its proximal end in alignment with lens 6. As shown in FIG. 1, the proximal end of channel may be longitudinally slotted to provide fingers 14 which flex radially inwardly to grip the proximal end of fiber 8. Also as shown in FIG. 1, the proximal ends of fingers 14 may be bent radially inwardly to act as longitudinal abutments for the proximal end of fiber 8. This arrangement also permits different types of fibers, e.g. fibers with tapered of untapered distal ends, in a single handpiece.

Fiber 8 may have an overall length of 5 cm, including a straight proximal portion 20 with a length of 1.5 cm, an arcuate middle portion 22 with a length of 1.5 cm and a distal portion 24 with a length of 2 cm.

Handpiece 10 is completed by a delivery tube 28 connected to a supply of a suitable liquid, typically water for directing a stream of cooling liquid to the region receiving laser radiation.

Unless otherwise indicated below, the various treatments can be, performed using laser radiation pulses having a therefor energy level of 1-600 mJ, a repetition rate Of 1 Hz-1 kHz, and preferably 50 Hz, a pulse duration of 0.4-1 ms and an average energy level of 150-300 mJ. For vaporization or cutting operations, the laser radiation must be focussed to a small diameter spot and must be in the form of pulses, and simultaneous cooling must be effected, preferably with a liquid steam. Other types of operations are better performed with a defocussed beam which can be either pulsed or continuous and cooling is not essential.

According to one feature of the invention, the laser radiation is applied in linearly polarized form with a polarization P parallel to the surface being treated. When this type of polarization is employed, the effective reflectivity of the surface receiving the radiation varies with the angle of incidence which the radiation forms with the surface. Specifically, the reflectivity decreases as the angle of incidence increases up to an angle slightly less than 90°; as the reflectivity decreases, the proportion of radiation absorbed by the tissue, and hence the vaporization or cutting effect, increases. Thus, by proper orientation of the output end of fiber 8, the vaporization or cutting action can be finely controlled.

According to a second particularly valuable feature of the invention, the radiation delivery fiber 8 is tapered in the region adjoining its output, or distal, end. It has been found that if a suitable taper is imparted, laser radiation energy is emitted over the length of the tapered region and is thus spread out along an extended section of the region being treated. This is particularly advantageous for root canal widening, or shaping, operations. Without such taper, the radiation is concentrated at the output end of the fiber 8. Concentration of the radiation at the output end of the fiber is desirable for the other procedures described herein, for which a tapered fiber would not be used, but when widening a tooth canal, such contration would tend to produce a ledge, or notch, in the canal wall. Therefore, it is preferred to use a tapered fiber for such a canal widening procedure, and for other procedures to be described below in which the distal end of the fiber is inserted into a tooth canal, and to use an untapered fiber for the other procedures described herein.

The length of the tapered region and the degree of taper may be varied to achieve the desired output distribution. Typically, a fiber 8 for performing a particular operation may have a working length, i.e. distal portion 24 extending out of handpiece 10, corresponding to the length of a mechanical file currently used for the same operation and a part of the distal portion, which part will in most cases extend from the distal end of fiber 8, may be tapered in accordance with the invention. By way of example distal portion 24 may have a length of 20 mm and may taper over the distal 16-20 mm of length thereof from a diameter of 600μ to a diameter of 200μ. Such taper may be linear. However, other degrees and types of taper may prove desirable for certain purposes.

For this procedure, the laser operating parameters should be adjusted to produce an average energy level of 150-250 mJ. The canal widening procedure described above will be facilitated by staining the canal wall a dark color before inserting the fiber. This can be achieved by introducing a substance such as silver nitrate into the canal.

Further, lasers according to the invention may include a reflective coating, e.g., of silica, upstream of the tapered distal portion to confine the radiation within the fiber 8 until it reaches the tapered distal portion.

According to a further advantageous feature of the invention, an optical fiber 8, which may be tapered as described above, is made of a low melting point composition, e.g., glass and a plastic, so that energy transmitted by the laser radiation acts to melt the fiber 8 to allow it to completely fill and seal a tooth or bone cavity while bonding to the cavity walls.

Such an operation may be performed to close a tooth canal, which is the last step in an endodontic procedure. This operation can be performed in a manner to close, or seal, a tooth canal to the region of the foramen, or apex. However, the operation can be employed to fill any type of cavity in tooth, i.e., enamel or dentin, or bone material.

Preferably, the low melting point composition has a melting temperature no higher than 800° C. Above that temperature, there is a likelihood of thermally produced tissue damage or trauma. Since the fiber 8 is composed primarily of silica, it is quite compatible with enamel, dentin and bone. The plastic is used only to create a suitable low melting temperature. Therefore, any plastic which will be compatible with the physiological tissue in question would be suitable. As a practical matter, the melting point of the composition should be no lower than 100° C.

Optical fibers having melting points at 150° C. and above are marketed by Fiberguide and General Fiber Optics, both of whom are located in New Jersey.

Before inserting the fiber in the tooth canal to be sealed, the canal wall can be stained to a dark color, e.g. with silver nitrate, to enhance the transmission of energy to the canal wall.

The benefits offered by a low melting point fiber 8 can be enhanced by applying a coating to the fiber surface in the region which is to be melted, the coating having a composition which will be melted by the laser radiation to form part of the filling. The ingredients of this coating can be selected to achieve a variety of goals. For example, the coating may contain one or more of:

a dark material, such as carbon black, which is highly absorptive of the laser radiation and thus will facilitate melting of the coating in response to a low radiation energy level;

a ground calcium phosphate material, such as hydroxyapatite, which is a natural component of every mineralized tissue in the body, including bone, enamel, dentin and cementum, and which can serve as a filler which acts to improve biological acceptance, or bodily toleration, of the glass/plastic composition;

ground ceramic which functions primarily as an inert filler; and/or any other composition compatible with the tissue being filled.

In the prior art, such materials were employed to fill dental cavities simply by being mechanically packed into the cavity, possibly together with a binder. By filling a cavity with a fused glass body, or a fused glass matrix containing various combinations of the above ingredients, according to the invention, a more complete filling of the cavity and bonding to the cavity walls are achieved.

To be able to heat the fiber 8 to melting temperature, it is sufficient to supply radiation at an average energy level of 50–200 mJ, the radiation being either continuous or pulsed. The thickness of the coating may be up to one-half the diameter of fiber 8. To achieve improved contact between the filling material and the canal walls, fiber 8, whether coated or uncoated, is subjected to a gentle longitudinal compression force while radiation is being supplied.

A cavity or opening in tooth or bone material can also be filled by forming a paste of a powder mixture containing one or more of the ingredients described above and a liquid, such as $H_3PO_4$, which will react with an ingredient of the mixture, e.g. hydroxyapatite, applying the paste to the region to be filled or sealed, and supplying laser radiation to the paste. Here again, a dark substance can be included in the paste to increase its energy absorption efficiency.

According to another feature of the invention, a filling or coating is formed by projecting a mixture of ingredients of the type referred to above into a cavity or recess to be filled or against a surface to be coated while supplying laser radiation via an optical fiber to promote a photochemical reaction which forms a hard, non-porous, durable mass which is bonded to the physiological tissue. The tissue in question can, again, be enamel, dentin or bone.

When forming fillings or coatings in this manner, the ingredients which are to react may all be delivered together if they will not react in the absence of the laser radiation; otherwise the components which will react are projected from two separate sources in a manner to be mixed together and to be exposed to laser radiation while traveling to the target surface. Preferably, the projection system is arranged so that the photochemical reaction begins while the ingredients are in flight and finishes after the ingredients contact the target surface.

Figure 2:
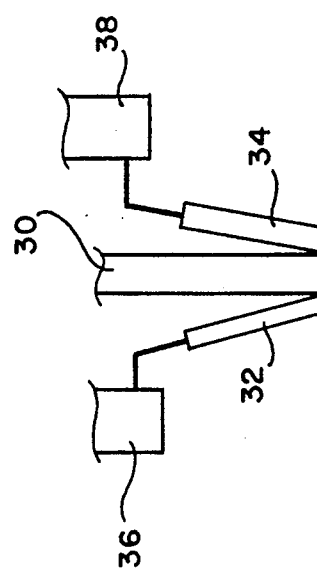
FIG. 2 is a view similar to that of FIG. 1 of a second device constructed to perform various treatments according to the invention.

The basic components of one arrangement of this type are shown in FIG. 2 and include an optical fiber 30 for conducting laser radiation to a region to be filled or coated, and two supply tubes 32 and 34 each connected to receive components of the coating or filling material from a respective supply unit 36 or 38.

To cite one example of a method carried out with the aid of the arrangement of FIG. 2, a mixture of materials of the type listed earlier herein, such as hydroxyapatite, ceramic and a dark colored material, e.g., carbon black, all in powdered form, is projected from tube 32 by being entrained in an air stream, while $H_3PO_4$ is projected from tube 34 by being entrained in a second air stream. The two streams mix together in a region illuminated by reaction-producing laser radiation emanating from fiber 30 and react to form calcium phosphate. Depending on the ingredients of the mixture, the reaction product could be monobasic calcium phosphate, $Ca(H_2PO_4)_2.H_2O$, dibasic calcium phosphate, $CaHPO_4.2H_2O$, or tribasic calcium phosphate, $CaO(OH)_2.(PO_4)_6$.

For this procedure, the laser radiation is preferably defocussed to cover the region across which the filling or coating is to be formed. Therefore, the radiation may be continuous or pulsed and a cooling stream is not required.

According to another aspect of the invention, the ability of Nd:YAG laser radiation to vaporize dark material is utilized to selectively destroy bacteria which may be present on tooth or gum surfaces and which will, if undisturbed, cause decay or infection. According to the invention, bacteria to be eliminated is stained to a dark color with a selective stain and is then exposed to a relatively low energy laser radiation which is sufficient to vaporize the bacteria.

By way of nonlimiting example, bacteria may be stained with methylene blue, dye agaroses, trypan blue, nigrosin, or naphtol blue black. Nigosin will stain bacteria black. These dyes can be used to stain, among others, staphylococcus, streptococcus, veillonella flora, and bacteroides melanogenicus.

As a result of such dark staining, such bacteria can be destroyed by application of laser radiation at a very low energy level. For example, the desired result can be achieved by applying laser radiation at an energy level of 2-10 mJ in the form of pulses having a repetition rate of 50 Hz and a pulse duration of 0.8 ms for a total time of 3-4 sec. When these parameters are established, destruction, i.e. vaporization, of the bacteria is achieved without in any way affecting the tissue on which the bacteria is present.

Without such staining, achievement of a similar result would require an energy level of the order of 100 mJ.

As mentioned above, procedures according to the present invention can be utilized for creating fillings or coatings in bone material. Since bone has a composition quite similar to that of tooth tissues, the filling and coating procedures described above could be employed. For example, a filling or coating could be formed by applying a powered mixture of hydroxyapatite and ceramic together with phosphoric acid, and applying laser radiation to produce a photochemical reaction which forms a fused mass composed of a form of calcium phosphate. A darkening agent, as described above, could be added to either component in order to reduce the level of energy needed to effect fusion. The addition of such dark material would allow the required energy level to be no higher than 200 mJ.

It is also possible to include in the powder mixture 50-60% by weight of natural bone material, the balance being made up of hydroxyapatite and ceramic. The components in question could be applied in the form of a paste or could be projected by a system of the type illustrated in FIG. 2.

In order to satisfactorily cut bone material with laser radiation, it is important to simultaneously apply to the radiation site a cooling liquid, preferably water, in order to prevent charring of the bone material. Water will not directly absorb energy from laser radiation having a wavelength of $1.06\mu$, but will remove heat absorbed by the bone material in order to prevent charring.

To perform the above-described procedures, use can be made of radiation from other types of lasers if the radiation is of a wavelength which is strongly absorbed by mineralized tissue but not significantly absorbed by water. In this case, for example, use could be made of Holmium lasers, Excimer lasers, or titanium-sapphire lasers, for example. Titanium-sapphire lasers offer the advantage of being tunable so that a single laser may be tuned, for example, to emit radiation either at a wavelength in the vicinity of 760 nm, which has been found most suitable for cutting soft physiologic tissue, or at a wavelength in the vicinity of $1\mu$, which has been found most suitable for cutting hard, or mineralized, physiologic tissue.

According to a further feature of of the invention, focussed laser radiation having the wavelength, energy level, pulse duration and pulse repetition rate described above can be applied to destroy, i.e. vaporize, tartar and calculus, particularly around a tooth root at or slightly below the gum line. At the same time, the radiation will act to vaporize necrotic cementum in the region being treated, sterilize the remaining cementum, and fuse dentine underlying the cementum in order to close tubules in the dentin and thus reduce hypersensitivity of this region of the tooth. For these operations, the preferred energy level is 200-300 mJ. While the radiation is being applied, a cooling liquid is delivered to the region being irradiated in order to protect the tooth tissue against charring.

While the description above refers to particular embodiments of the present invention, it will be understood that many modifications may be made without departing form the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of cutting physiologic tissue in the mouth of a patient, comprising:

providing a tunable laser which is tunable to produce laser radiation at any one of at least two different wavelengths, including a first wavelength which is effective for cutting physiologic tissue of a first type and a second wavelength for cutting physiologic tissue of a second type;

tuning the laser to produce radiation at one of the first and second wavelengths;

emitting the radiation being produced by the laser and directing the emitted radiation at physiologic tissue of the type corresponding to the radiation wavelength which the laser is tuned to produce; and at least when the laser is tuned to produce radiation at a selected wavelength, directing a cooling liquid at the physiologic tissue at which the emitted radiation is being directed simultaneously with performance of said directing step.

2. A method as defined in claim 1 wherein the tissue of a first type is hard physiologic tissue and the tissue of the second type is soft physiologic tissue, and said step of directing a cooling liquid is performed when the laser is tuned to produce radiation at the first wavelength.

3. A method as defined in claim 2 wherein the first wavelength is in the vicinity of $1\mu$ and the second wavelength is in the vicinity of $760\mu$.

4. A method as defined in claim 3 wherein the laser is a titanium sapphire laser.

5. A method as defined in claim 4 wherein said step of emitting comprises emitting the radiation in the form of pulses.

6. A method as defined in claim 5 wherein said steps of emitting and directing comprise focusing the emitted radiation to a small diameter spot on the physiologic tissue.

7. A method as defined in claim 1 wherein the first wavelength is in the vicinity of $1\mu$ and the second wavelength is in the vicinity of $760\mu$.

8. A method as defined in claim 7 wherein the laser is a titanium sapphire laser.

9. A method as defined in claim 1 wherein said step of emitting comprises emitting the radiation in the form of pulses.

10. A method as defined in claim 9 wherein said steps of emitting and directing comprise focusing the emitted radiation to a small diameter spot on the physiologic tissue.

* * * * *